United States Patent [19]

Lamplough

[11] Patent Number: 5,817,301

[45] Date of Patent: Oct. 6, 1998

[54] HAIR DYE COMPOSITION

[75] Inventor: Alan John Lamplough, Long Eaton, United Kingdom

[73] Assignee: S Products Limited, Edinburgh, Scotland

[21] Appl. No.: 687,380

[22] PCT Filed: Feb. 6, 1995

[86] PCT No.: PCT/GB95/00234

§ 371 Date: Sep. 25, 1996

§ 102(e) Date: Sep. 25, 1996

[87] PCT Pub. No.: WO95/20941

PCT Pub. Date: Aug. 10, 1995

[30] Foreign Application Priority Data

Feb. 5, 1994 [GB] United Kingdom .................... 9402225

[51] Int. Cl.⁶ ........................................................ A61K 7/13
[52] U.S. Cl. ............................................................. 424/70.1
[58] Field of Search ............................................. 424/70.1

[56] References Cited

U.S. PATENT DOCUMENTS

| | | | |
|---|---|---|---|
| 3,683,942 | 8/1972 | McKay | 132/112 |
| 4,147,750 | 4/1979 | Geria et al. | |
| 4,322,400 | 3/1982 | Yuhas | 424/65 |
| 4,617,185 | 10/1986 | DiPietro | 424/65 |
| 4,695,452 | 9/1987 | Gannis et al. | |
| 5,431,906 | 7/1995 | Mohseni et al. | 424/70.1 |

FOREIGN PATENT DOCUMENTS

| | | |
|---|---|---|
| 0 117 070 | 8/1984 | European Pat. Off. |
| 0 222 525 | 5/1987 | European Pat. Off. |
| 51-110046 | 3/1975 | Japan ................................. 424/70.1 |
| 749045 | 5/1956 | United Kingdom . |
| 1288128 | 2/1969 | United Kingdom . |
| 2019446 | 4/1979 | United Kingdom . |
| WO 92/15280 | 9/1992 | WIPO . |

OTHER PUBLICATIONS

JP59021608, *Patent Abstracts of Japan*, vol. 8, No. 106 (C–223).

*Primary Examiner*—Peter F. Kulkosky
*Attorney, Agent, or Firm*—Bell Seltzer Intellectual Property Group of Alston & Bird LLP

[57] ABSTRACT

The present invention provides a long-lasting hair colourant composition comprising an intimate admixture of a dye with a phsiologically acceptable compatible solid base. The stick has a hardness which is sufficiently high to provide substantial dimensional stability under light to moderate manual pressure under ambient temperatures and sufficiently low to allow easy gliding of the stick over a mass of damp hair and transfer of stick material thereto under light to moderate manual pressure. The stick also contains an effective lathering component and is substantially free of alkaline soap material.

12 Claims, No Drawings

HAIR DYE COMPOSITION

The present invention relates to long-lasting hair dye compositions and in particular to the presentation of such compositions in solid stick form.

Conventional long-lasting hair dye compositions are generally presented in the form of a more or less thick liquid which is poured onto the hair mass, rubbed into the hair mass to distribute it through the hair mass, and then allowed to act on the hair for an extended period of time, perhaps 30 to 60 minutes depending on the dye and the temperature, to allow the dye to attach to the hair. In general the higher the temperature the shorter the time period required, thus the hair mass may, for example be covered over by a cap to trap body heat in it, or subjected to heating from a hot air blower. The residual composition is then washed out of the hair.

These known compositions are, however, somewhat awkward to apply and considerable care is required to avoid the dye running down the subject's head and possibly onto his/her clothes. Also care is required in order to obtain either a reasonably even distribution or a heavier application in specific sections of the hair mass for any desired special effect and/or to even out an existing unevenness in colouring.

It has also previously been proposed to provide pasty stick or slab compositions for dyeing hair which the dyestuff is encapsulated in micro-capsules to prevent deterioration thereof prior to use, the dyestuff being released by bursting of the micro-capsules by pressing the stick against the hair to be dyed. A problem with this approach is however that the effectiveness of the dye application depends on the successful bursting of the microcapsules which in turn depends on adequate pressure being exerted by pressing hard enough against the body underlying the hair mass to be dyed. A further problem is that the surface layer of the stick will retain a quantity of broken micro-capsules and the dye released therefrom which have not been transferred to the hair mass. The dyestuff is of course no longer protected against deterioration and the surface layer will then tend to undergo various undesirable changes dye to interaction of the stick base with the dye, interaction of dye and/or other different components released from different micro-capsules, and/or interaction of the contents of the micro-capsules with the atmosphere.

It is an object of the present invention to avoid or minimise one or more of the above disadvantages.

The present invention provides a long-lasting hair colourant stick composition comprising an intimate admixture of a direct dye with a physiologically acceptable compatible solid base having a hardness which is sufficiently high to provide substantial dimensional stability under light to moderate manual pressure under ambient temperatures and sufficiently low to allow easy gliding or the stick over a mass of damp hair and transfer of stick material thereto under light to moderate manual pressure, and containing a effective lathering component, whilst being substantially free of alkaline soap material.

It will be understood that the hardness of such a composition can be measured by various methods generally known in the part. Preferably the stick composition has a hardness in the range from 4 to 8 Newtons when measured by the following method. An Instron Universal Testing Instrument 1122 (normally used for testing the hardness of stick compositions such as lipstick) was employed with a steel probe having a diameter of 7 mm. The stick composition is placed in a holder and the probe advanced towards the stick at a rate of 50 mm/minute. When the probe tip contacts the surface of the stick composition it experiences a resistance to continued forward movement requiring the probe driving force to be increased. This force continues to increase to a peak when the probe breaks-through into the interior of the stick composition and this initial peak is used to provide a measure of the hardness of the stick composition.

As used herein the term "compatible" means that the solidifying medium should not have a significant adverse effect on the performance and functioning of the hair dye, in particular in relation to its colour, its effective life both on the shelf and in the hair i.e. it should be able to withstand substantially at least several hair washes, and non-colouring of the scalp or skin generally.

Various suitable materials commonly used in cosmetic stick compositions e.g. deodorant sticks, may be used in order to achieve the desired hardness parameters. A principal component is conveniently a higher alkyl carboxylic fatty acid e.g. palmitic acid or oleic acid, but most preferably stearic acid. This should however be used together with an effective amount of a hardness control agent. It has been found that the hardness of the stick composition depends on the fatty acid and amount thereof used. Various suitable hardness control agents may be used to bring the hardness of the solid base within the desired range.

In general there is used a substance which is substantially miscible with the substantially non-water soluble stearic acid. Conveniently there is used a long chain aliphatic alcohol or derivative thereof such as, for example, one or more of cetyl alcohol, stearyl alcohol, glycol stearate, and coconut mono-ethanolamide.

A particularly suitable hardness control agent which is reasonably economic, does not significantly impair the colouring or permanence properties of the dye component (c), is not excessively volatilized in use (unlike lower alkyl alcohols such as ethanol), and minimizes adhesion of the stick to its container or holder, is cetyl alcohol.

In order to facilitate application and spreading of the composition to and through the wet mass of hair there is normally also included an effective amount of an emulsifier, preferably an oil-in-water emulsifier such as for example Ceteth 20 (available from Crode Chemicals under the Trade Name Cetomacrogol) although various other emulsifiers known in the art could also be used. Preferably there is used from 1 to 10, advantageously from 2 to 5% w/w of emulsifier.

The new stick compositions of the present invention can be readily applied to a wetted head of hair by simply drawing the stick over the hair as required. It will be appreciated that the application of the hair colourant is particularly easy and convenient to control as the stick can be drawn over different parts of the hair mass as many times as may be required for any given part of the hair mass, without the risk of a liquid composition running down the subject's neck etc.

Once the required amount of composition has been applied, it can be rubbed into the hair mass (with additional moistening of the hair if required e.g. by spraying on some water) to work it into the hair mass. As noted hereinbefore, the stick composition of the present invention includes a lathering component which may conveniently be in the form of a shampoo-type base which can be worked up into a lather by the rubbing in at this stage. A suitable lathering component that may be mentioned is ammonium lauryl sulphate, though various other detergents may also be used including anionic and cationic detergents may also be used including anionic and cationic detergents, and tallow based surfactants, care being taken to ensure compatibility with the dye components being used. Conveniently there is used from 2.5 to 18% w/w, preferably from 8 to 14.5% w/w, of the lathering component. The composition is then left in place for some time to allow the dye component(s) to become attached to the hair. The required time will depend on factors such as the particular dye components used and the temperature, increased temperatures generally requiring less time as noted hereinabove. Suitable times will generally be in the range from 20 to 60 minutes or so. The residual composition can then be washed out in the normal way and the hair dried.

Various dyes may be used in the stick compositions of the present invention. In general these are so-called "direct" dyes which bond physically e.g. electrostatically to the hair fibres, without the need for any chemical reaction, e.g. oxidation, taking place, and can produce a semi-permanent colouring of the hair which can withstand several hair-washed before substantial loss of colour occurs. Various suitable direct dyes are known in the art including so-called dispersed dyes, acidic dyes, and basic dyes. Dispersed dyes and acidic dyes are usually preferred for their better compatibility with the usual lathering agents.

The amount of solid base may be varied according to the final consistency and ease of application required and will also depend on the nature of the liquid dye composition used and the intensity of dyeing required, and the particular solid base used. In general the stick compositions of the invention may contain from 10 to 90% w/w, preferably from 50 to 80% w/w of the liquid hair dye composition (including any shampoo-type base etc), and form 15 to 90% w/w, preferably 30 to 70% w/w of the solid base.

It will be appreciated that various liquid hair dye compositions which are readily available commercially, may be used in the stick compositions of the present invention. These may include various conventionally employed materials as desired such as for example chelating agents such as EDTA to minimise scum formation when the composition is used with hard water and/or heavily mineralised water; emulsifying and/or stabilising agents such as ethoxydiglycol; additional surfactants e.g. tallow based sufactants such as Lowenol 1985 ™ available for Lowenstein Dyes & Cosmetics Inc. of New York, U.S.A; and thickening agents such as chemically modified cellulose polymers e.g. Cellow 940 ™ also available from Lowenstein. The amount of individual due(s) used will generally depend on the intensity of colouring required. If desired some water can be included to facilitate incorporation of the dye into the composition, and/or to help "dilute" the intensity of the colouring produced by the dye.

Other suitable ingredients may also be incorporated in the compositions of the present invention in generally known manner. Thus, for example, there may be included a physiologically acceptable preservative. Suitable preservatives that may be mentioned include "Kathon" ™ which comprised methyl chloroisothiazolinone, methyl isothiazolinone, and magnesium nitrate; or a mixture of methyl paraben and propyl paraben. Advantageously there may also be included an enhancing agent such as dimethicone (dimethyl polysiloxane) which improves shine in the hair and the vibrancy of the colouring thereof. In order to increase the uptake of dye into grey hair under the non-alkaline conditions encountered with the stick compositions of the present invention, there may advantageously be included a hair welling agent such as urea. Preferably this is used in an amount of from 2 to 6% preferably about 5% w/w.

The compositions of the invention may be prepared by any suitable method known in the art. Conveniently the hardening medium component(s) is (are) heated to an elevated temperature at which it is (they are) substantially fluid without being adversely affected e.g. from 55° to 70° C., and homogenized if required. The other ingredients are then added at a generally similar elevated temperature and thoroughly mixed in. The resulting mixture may be cooled slightly, e.g. to around 50° to 60° C., and then poured into a suitable mould or directly into a holder or container for the stick, and allowed to cool and solidify.

Further preferred features and advantages of the present invention will appear from the following examples given by way of illustration only.

EXAMPLE 1

Preparation of Hair Dye Stick Composition

A 100 g composition was prepared with the following composition:

| | |
|---|---|
| Stearic Acid | 45 g |
| Cetyl Alcohol | 15 g |
| Methyl Paraben | 0.2 g |
| Propyl Paraben | 0.2 g |
| Ammonium Lauryl Sulphate | 12 g |
| HC Blue No2 Dispersed Dye | 20 g |
| Purified Water | up to 100 g |

The stearic acid was melted at around 70° C. The other ingredients were all mixed together and also heated to about 70° C. Whereupon the hot molten stearic acid was added slowly with stirring. Mixing was continued for about 10 to 15 minutes and the resulting mixture cooled, while still stirring, to about 50° to 60° C. whereupon it was introduced into a generally cylindrical mould or holder and allowed to cool to ambient temperature to form a solid stick.

EXAMPLE 2

Use of hair Dye stick

The hair dye stick produced in Example 1 was stroked over a pre-wetted head of hair until a visible amount of the composition had been applied across substantially the whole of the hair mass. A small amount of water was then sprayed onto the hair and the composition was then gently rubbed in for 3 to 4 minutes building up a substantial lather. The hair mass was heated with a hair dryer for about 2 minutes, and then rinsed in warm water. The hair was then shampoo-washed in the normal way and towelled dry.

EXAMPLE 3

Hair Dye Stick Compositions

A 100 g stick composition was prepared with the following composition:

| | |
|---|---|
| Stearic Acid | 40.6 g |
| Cetyl Alcohol | 9.1 g |
| Cetomacrogol 1000 BP | 2.2 g |
| Ammonium Lauryl Sulphate | 29.9 g |
| HC Blue No2 Dispersed Dye | 2 g |
| Silicone Fluid Fill/300 | 1 g |
| Methylhydroxybenzoate | 0.2 g |
| Propylhydroxybenzoate | |
| Purified Water | 15 g |

The stearic acid, cetyl alcohol and cetomacrogol were melted together at around 70° C. The ammonium lauryl sulphate and water were separately heated to 70° C. and then mixed into the stearic acid mixture. The other ingredients were all then mixed in while keeping the teperature at about 70° C. Mixing was continued for about 10 to 15 minutes and the resulting mixture cooled, while still stirring, to about 50° to 60° C. whereupon it was introduced into a generally cylindrical mould or holder and allowed to cool to ambient temperature to form a solid stick.

I claim:

1. A hydrous hair colorant stick composition comprising an admixture of:

a hair dye, and a solid base comprising from 1 to 30% w/w of said base of a hardness control agent selected from the group consisting of cetyl alcohol and a glycol and the remainder being a member selected from the group consisting of palmitic acid, oleic acid and stearic acid; and an effective amount of lathering component, said hydrous hair colorant stick being substantially free of alkaline soap material, said composition containing at least about 15 percent water.

2. The hydrous hair colorant stick composition according to claim 1 wherein said lathering component is from 2.5 to 18% w/w of said stick.

3. A hydrous hair colorant stick composition comprising an admixture of:

a hair dye, and a solid base comprising from 1 to 30% w/w of said base of cetyl alcohol and the remainder being stearic acid; and from 2.5 to 18% w/w of a lathering component, said hydrous hair colorant stick being substantially free of alkaline soap material, said composition containing at least about 15 percent water.

4. The hair colorant stick composition according to claim 3 wherein cetyl alcohol is present in an amount of about 15% w/w, stearic acid is present in an amount of about 45% w/w, and said lathering component is ammonium lauryl sulfate in an amount of about 12% w/w.

5. The hair colorant stick composition according to claim 3 wherein cetyl alcohol is present in and amount of about 9.1% w/w, stearic acid is present in an amount of about 40.6% w/, and said lathering component is ammonium lauryl sulfate in an amount of about 29.9% w/w.

6. A hydrous hair colorant stick composition comprising an admixture of:

a hair dye, and a physiologically acceptable compatible solid base comprising;

from 1 to 30% w/w of said base of hardness control agent selected from the group consisting of a long-chain aliphatic alcohols or derivative thereof as a hardness control agent and the remainder being a higher alkyl carboxylic fatty acid; and an effective amount of a lathering component, said hydrous hair colorant stick being substantially free of alkaline soap material, said composition containing at least about 15 percent water.

7. The hair colorant stick composition according to claim 6, wherein said lathering component is from 2.5 to 18% w/w of said stick.

8. The hair colorant stick composition according to claim 6 wherein said higher alkyl carboxylic fatty acid is selected the group consisting of palmitic, oleic and stearic acids.

9. The hair colorant stick composition according to claim 6 wherein said long-chain aliphatic alcohol is a selected from the group consisting of cetyl alcohol, stearyl alcohol, glycol stearate and coconut mono-ethnolamide.

10. The hair colorant stick composition according to claim 6 further comprising from 1 to 10% w/w of an emulsifier.

11. The hair colorant stick composition according to claim 6 further comprising a preservative.

12. The hair colorant stick composition according to claim 6 further comprising from 2% to 6% of w/w of a hair swelling agent.

* * * * *

UNITED STATES PATENT AND TRADEMARK OFFICE
CERTIFICATE OF CORRECTION

PATENT NO.  : 5,817,301
DATED       : October 6, 1998
INVENTOR(S) : Alan John Lamplough It is certified that error appears in the above-identified patent and that said Letters Patent is hereby corrected as shown below:

On the title page, item [73] Assignee should read --Solid Products Limited, Edinburgh, Scotland--.

In the References Cited, FOREIGN PATENT DOCUMENTS, line 3, "3/1975" should read --9/1976--.

In the Abstract, line 3, "phsiologically" should read --physiologically--.

Column 5, line 14, after "of" insert --a--.

Column 6, line 10, after "of", insert --a--; line 11, after "of" omit "a".

Signed and Sealed this

Sixth Day of July, 1999

Attest:

Q. TODD DICKINSON

*Attesting Officer*   *Acting Commissioner of Patents and Trademarks*